United States Patent
Subramaniam

(10) Patent No.: US 11,291,809 B2
(45) Date of Patent: Apr. 5, 2022

(54) IMPLANTABLE SHUNT SYSTEM AND METHOD

(71) Applicant: Thirusivapragasam Subramaniam, Rochester, MN (US)

(72) Inventor: Thirusivapragasam Subramaniam, Rochester, MN (US)

( * ) Notice: Subject to any disclaimer, the term of this patent is extended or adjusted under 35 U.S.C. 154(b) by 0 days.

(21) Appl. No.: 17/299,055

(22) PCT Filed: Jan. 16, 2020

(86) PCT No.: PCT/US2020/013816
§ 371 (c)(1),
(2) Date: Jun. 2, 2021

(87) PCT Pub. No.: WO2020/150433
PCT Pub. Date: Jul. 23, 2020

(65) Prior Publication Data
US 2021/0353921 A1      Nov. 18, 2021

Related U.S. Application Data

(60) Provisional application No. 62/794,210, filed on Jan. 18, 2019.

(51) Int. Cl.
*A61M 27/00* (2006.01)
(52) U.S. Cl.
CPC ... *A61M 27/006* (2013.01); *A61M 2205/3334* (2013.01); *A61M 2205/3344* (2013.01)

(58) Field of Classification Search
CPC ............ A61M 27/006; A61M 25/0026; A61M 2025/0039
See application file for complete search history.

(56) References Cited

U.S. PATENT DOCUMENTS

| 5,385,541 | A | 1/1995 | Kirsch et al. |
| 5,522,807 | A | 6/1996 | Luther |
| 7,309,330 | B2 | 12/2007 | Bertrand et al. |
| 9,364,674 | B2 | 6/2016 | Cook et al. |
| 2005/0284815 | A1 | 12/2005 | Sparks et al. |
| 2008/0249501 | A1 | 10/2008 | Yamasaki |
| 2015/0157784 | A1 | 6/2015 | Santora et al. |
| 2018/0056050 | A1 | 3/2018 | Degen et al. |

OTHER PUBLICATIONS

International Preliminary Report on Patentability for Parent PCT Application, dated Dec. 28, 2020.

*Primary Examiner* — Leslie R Deak
(74) *Attorney, Agent, or Firm* — Diament Patent Law, P.C.; Adam Diament

(57) ABSTRACT

The present invention provides a novel shunt device and methods of use, and in particular a cerebral shunt device. The cerebral shunt device includes an outer tube member forming a first lumen, the outer tube member having a drainage outlet and at least one opening to the first lumen in a distal region along the length of the outer tube member. The shunt also includes an inner tube member forming a second lumen, the inner tube member having at least one opening to the second lumen along the length of the inner tube member. The inner tube member is positioned within the first lumen and a pump unit fluidly connected to the second lumen to force fluid from the first lumen, which clears obstructions in the shunt.

5 Claims, 5 Drawing Sheets

500

510 — inserting the distal region of a cerebral shunt into the cerebral ventricle of a subject 520 — positioning the drainage holes of the outer lumen tube within a region of the ventricle space 530 — drawing CSF through the outer lumen openings and into the outer lumen 540 — Activating the pump unit to generate a pressure within the inner and outer lumens of the device to push the CSF out into the outer lumen by creating a high pressure in the inner lumen. This process will push the debris and the choroid plexus away from the pores on the outer lumen thus preventing the blockage.

550 — deactivating the pump unit to reduce pressure and permit drawing CSF through the outer lumen openings and into the outer lumen

Fig. 4

IMPLANTABLE SHUNT SYSTEM AND METHOD

CROSS REFERENCE TO RELATED APPLICATIONS

This application is a National Stage application under 35 U.S.C. § 371 of PCT Application No. PCT/US2020/013816, filed Jan. 16, 2020, which claims benefit of U.S. Provisional Patent Application No. 62/794,210, filed Jan. 18, 2019, entitled, "Implantable Shunt System and Method." The contents of each are incorporated by reference in their entireties.

FEDERALLY SPONSORED RESEARCH OR DEVELOPMENT

None.

FIELD OF DISCLOSURE

The present invention relates to implantable shunt systems, and more specifically, to a shunt system for draining cerebrospinal fluid.

BACKGROUND

Hydrocephalus is the excessive accumulation of cerebrospinal fluid (CSF) in the brain. It affects a wide range of people from infants to older children to young middle aged and older adults. In fact, over one million people in the United States live with hydrocephalus. For every 1000 babies born in the US, one or two will have hydrocephalus, and it is the most common reason for brain surgery in children.

There are two kinds of hydrocephalus: congenital hydrocephalus and acquired hydrocephalus. Congenital hydrocephalus is present at birth and may be caused by a genetic defect, or other issues during development in utero. An unusually large head is the primary indication of congenital hydrocephalus. Acquired hydrocephalus can occur at any age and may be caused by head injuries, strokes, infections, tumors and bleeding in the brain. Symptoms of acquired hydrocephalus can include headache, vomiting and nausea, blurry vision, balance problems, bladder control problems, thinking and memory problems.

Hydrocephalus can permanently damage the brain, causing problems with physical and mental development. If untreated, it is usually fatal. Treatment usually involves surgery to insert a shunt.

Surgical interventions for the treatment of hydrocephalus generally involves the placement of a ventricular catheter, for instance a tube made of silastic, into the cerebral ventricles of a patient in order to bypass an obstruction in flow of CSF or to bypass malfunctioning arachnoidal granulations. The catheter can then drain the excess fluid into other body cavities, from where it can be resorbed. Most shunts drain the fluid into the peritoneal cavity (ventriculoperitoneal shunt), but alternative sites include the right atrium (ventriculo-atrial shunt), pleural cavity (ventriculopleural shunt), and gallbladder. A shunt system can also be placed in the lumbar space of the spine and have the CSF redirected to the peritoneal cavity (lumbar-peritoneal shunt).

There are a number of complications associated with shunt placement. Many of these complications occur during childhood and cease once the patient has reached adulthood. Many of the complications seen in patients require immediate shunt revision (the replacement or reprogramming of the already existing shunt). The common symptoms often resemble the new onset of hydrocephalus such as headaches, nausea, vomiting, double-vision, and an alteration of consciousness. Furthermore, in the pediatric population, the shunt failure rate two years after implantation has been estimated to be as high as 50%.

The complications include infection, obstruction, over drainage and interventricular hemorrhage. Obstructions to flow through cerebral shunts are the primary source of complications. A cerebral shunt has a ventricular catheter portion, a valve portion, and a drainage catheter portion. Of the obstructions that occur within the shunt, generally 30.4% occur within the ventricular catheter portion, 11.7% occur within the valve portion, and 13.7% occur within the drainage catheter portion.

Current cerebral shunts generally have at least three components: a ventricular catheter, a valve, and a distal catheter. The valve in prior designs is placed to prevent backflow of CSF, which can cause infection. Often, the valve is a separate component attached between the ventricular catheter and the distal catheter. However, due to the inherent structural requirements, in particular the valve, obstructions can occur that block flow within the catheter.

Several shunts have been designed to attempt to resolve the blockage problems. U.S. Patent Pub. No. US20080249501, entitled, "Methods for simultaneous injection and aspiration of fluids during a medical procedure," to Yamaski et al, discloses a dual lumen constant volume aspiration catheter that injects a volume of injectable fluid to break up an obstruction within the brain or cranial subarachnoid space while simultaneously aspirating a same volume of aspirated fluid from the treatment site.

U.S. Pat. No. 5,385,541, entitled, "Cerebrospinal fluid shunt capable of minimal invasion revision," to Kirsch et al., discloses a surgical shunt capable of revision and inspection on a minimal invasive basis. The shunt allows a device to be externally inserted into the interior regions of the shunt in order to remove blockages and improve cerebrospinal fluid flow.

U.S. Pat. No. 5,522,807, entitled "Dual lumen infusion/aspiration catheter," to Luther, discloses a catheter having various slits in the walls of the catheter to open in response to increased fluid pressure to facilitate infusion.

U.S. Pat. No. 7,309,330, entitled "Implantable cerebral spinal fluid drainage device and method of draining cerebral spinal fluid," to Bertrand et al., discloses a drainage system that includes a ventricular catheter, a drainage catheter, and positive displacement pump that can function to actively drain CSF from the ventricles of the brain of a patient.

U.S. Patent Pub. No. US20180056050, entitled, "Implantable fluid management system having clog resistant catheters, and methods of using same," to Degan et al., discloses a system that cycles fluid through inlet catheters in predetermined time intervals to sensed conditions to minimize the risk that inlet catheters become clogged due to tissue growth or solid objects within accumulated fluid.

The contents of the above referenced patents and patent applications, as well as any subsequently cited patent, patent application, or non-patent literature document, is hereby incorporated by reference in their entireties, for all purposes.

However, there is still a need in the art for an improved ventricular catheter, and other shunt devices, for use in the correction of hydrocephalus that does not get blocked and/or significantly reduces the need for revision. The present embodiments address these needs.

SUMMARY

A cerebral shunt device is described. However, the shunt device may also be used in non-cerebral embodiments and may be used to remove or drain non-cerebral fluids from various tissues and/or organs and is more generally is any implantable shunt system and method of use.

The device includes an outer tube member forming a first lumen, the outer tube member having a drainage outlet and at least one opening to the first lumen in a distal region along the length of the outer tube member, an inner tube member forming a second lumen, the inner tube member having at least one opening to the second lumen along the length of the inner tube member, wherein the inner tube member is positioned within the first lumen, and a pump unit fluidly connected to the second lumen. In one embodiment, the inner and outer tube members are coaxial. In another embodiment, the at least one opening along the length of the outer tube member is larger than the at least one opening along the length of the inner tube member. In another embodiment, the at least one opening along the length of the inner tube member is sized to permit only the flow of a gas therethrough.

In another embodiment, the device further includes a valve positioned at the drainage outlet of the outer tube member. In another embodiment, the device further includes a controller communicatively connected to the pump unit and the drainage outlet valve. In another embodiment, the pump unit comprises an air pump. In another embodiment, the pump unit comprises a hydraulic pump. In another embodiment, the device further includes at least one pressure sensor. In another embodiment, the device further includes at least one flow sensor. In another embodiment, the outer tube member includes between 4 and 10 distal region openings to the first lumen positioned around the circumference of the outer tube member. In another embodiment, the inner tube member includes between 8 and 12 distal region openings to the first lumen positioned around the circumference of the outer tube member. In another embodiment, the distal region openings of the outer tube member have an average diameter of between 0.5 and 1 mm. In another embodiment, the distal region openings of the inner tube member have an average diameter of between 0.2 and 0.6 mm.

Also described is a method of removing cerebral spinal fluid (CSF) from a subject. The method includes the steps of inserting the distal region of the cerebral shunt device of claim 1 into the cerebral ventricle of a subject, positioning the at least one opening along the length of the outer tube member within a region of the ventricle space, and drawing CSF from the ventricle space through the at least one opening along the length of the outer tube member and into the first lumen. Upon determining that the at least one opening along the length of the outer tube member is obstructed, the method includes the steps of activating the pump unit to inject a fluid into the second lumen to generate enough pressure within the first lumen to force the fluid or CSF from the first lumen out through the at least one opening along the length of the outer tube member, thereby clearing the obstruction, and deactivating the pump unit to permit drawing CSF from the ventricle space through the at least one opening along the length of the outer tube member and into the first lumen. In some embodiments, the pump unit is activated at a set time interval.

A significant advantage of the present system and methods compared to current catheter systems is the lack of the requirement of a valve, which in present catheters is required to prevent backflow of CSF. In the present embodiments, a valve is not necessary because of the presence of a powered motor that activates a circulating member (turbine), forces fluid in one direction, thereby preventing backflow of the CSF from the distal catheter toward the ventricular catheter. Without a valve or circulating member, backflow would occur and cause infection from the abdomen via the distal catheter into the brain, which may lead to death.

BRIEF DESCRIPTION OF THE DRAWINGS

The foregoing summary, as well as the following detailed description of several embodiments will be better understood when read in conjunction with the appended drawings. It should be understood, however, that the invention is not limited to the precise arrangements and instrumentalities of the embodiments shown in the drawings. In the drawings:

FIG. 4 illustrates an exemplary method of implanting and using a cerebral shunt device;

DETAILED DESCRIPTION

Figure 1:
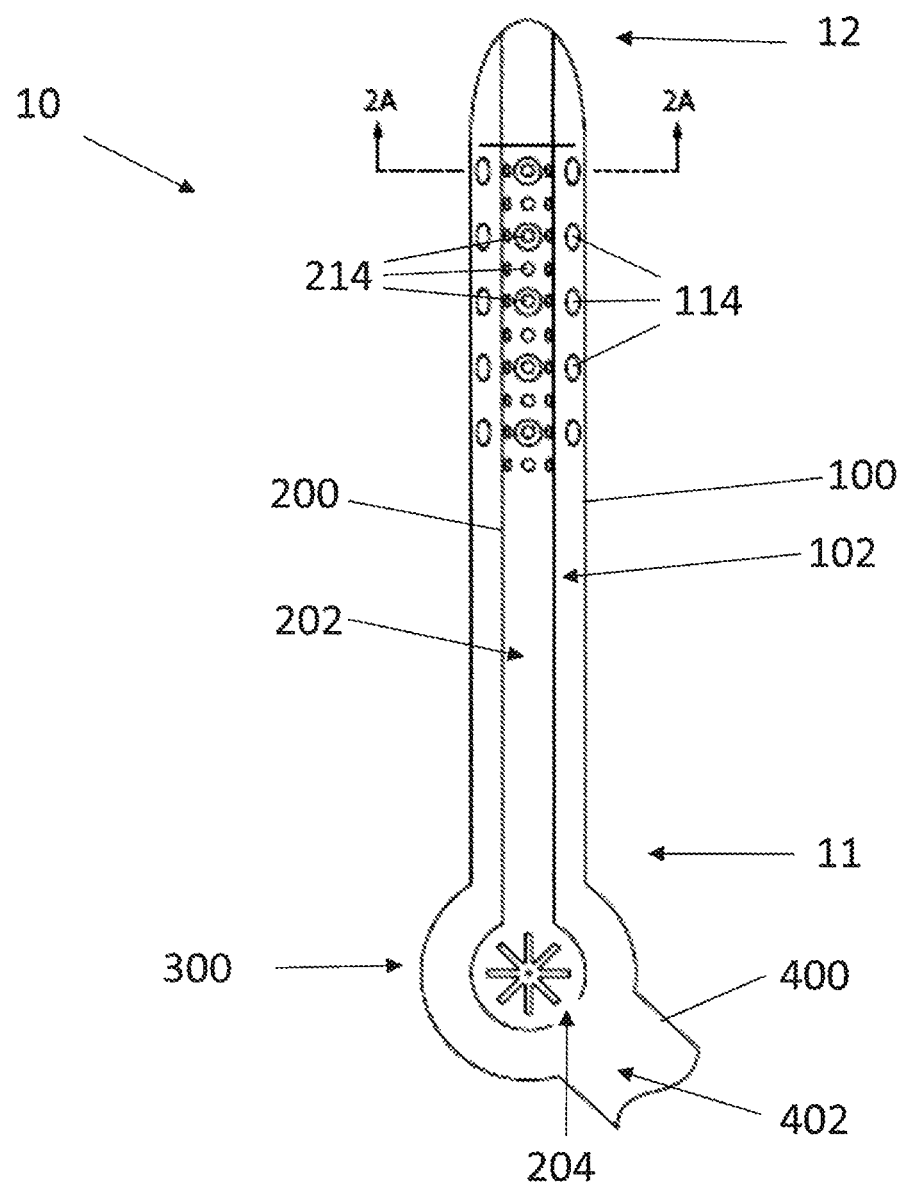
FIG. 1 is a side view an exemplary embodiment of the cerebral shunt device as described herein.

The present embodiments relate to a ventricular shunt for the treatment of hydrocephalus, and methods of use for improved drainage of CSF from a subject. The present embodiments also comprise novel systems and methods for clearing obstructions in order to maintain continuous flow of CSF from a subject.

Definitions

Unless defined otherwise, all technical and scientific terms used herein have the same meaning as commonly understood by one of ordinary skill in the art. Although any methods and materials similar or equivalent to those described herein can be used in the practice or testing of the present embodiments, preferred methods and materials are described. As used herein, each of the following terms has the meaning associated with it in this section.

The terminology used herein is for the purpose of describing particular embodiments only, and is not intended to be limiting of the invention. As used herein, the singular forms "a," "an," and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

"About" or "Substantially" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

Ranges: throughout this disclosure, various aspects of the embodiments can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, relative terms, such as "lower" or "bottom," "upper" or "top," "left" or "right," "above" or "below," "front" or "rear," may be used herein to describe one element's relationship to another element as illustrated in the Figures. It will be understood that relative terms are intended to encompass different orientations of the device in addition to the orientation depicted in the Figures.

It will be understood that when an element is referred to as being "on" another element, it can be directly on the other element or intervening elements may be present therebetween. As used herein, the term "and/or" includes any and all combinations of one or more of the associated listed items.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section.

It will be understood that the elements, components, regions, layers and sections depicted in the figures are not necessarily drawn to scale.

Exemplary embodiments are described herein with reference to idealized embodiments of the present invention. As such, variations from the shapes of the illustrations as a result, for example, of manufacturing techniques and/or tolerances, are to be expected. Thus, embodiments should not be construed as limited to the particular shapes of regions illustrated herein but are to include deviations in shapes that result, for example, from manufacturing. The embodiments illustratively disclosed herein suitably may be practiced in the absence of any elements that are not specifically disclosed herein.

Description

The present embodiments provide a novel shunt device and methods for draining fluid from bodily spaces, and in particular, draining cerebral spinal fluid from cerebral ventricles. The cerebral shunt device of the present invention prevents the blockage of fluid flow, thereby maintaining continuous removal of cerebral spinal fluid from the ventricular space of a subject. It should also be appreciated that the present invention is not limited to use as a drain of CSF, but rather may be used in any portion of the subject's body requiring drainage of a fluid, and particularly where the fluid to be drained includes larger particulates or debris that can clog or obstruct the primary drainage holes of a typical shunt, catheter or other drainage tube.

Referring now to FIG. 1, an exemplary cerebral shunt device 10 is shown. The cerebral shunt device 10 generally comprises an outer tube member 100, an inner tube member 200, and a pump unit 300. As shown, device 10 has a proximal end 11 and distal end 12. Outer tube member 100 forms an outer tube lumen 102 running along the length of device 10. Outer tube member 100 at proximal end 11 includes a drainage outlet and is connected to a drainage tube 400, such that outer tube lumen 102 is fluidly connected to the lumen 402 of drainage tube 400. Inner tube member 200 is positioned within lumen 102 and forms an inner tube lumen 202 also running along the length of device 10. In some embodiments, the proximal end of inner tube lumen 202 is fluidly connected to lumen 402 of drainage tube 400 through an opening 204. In some embodiments, there is no opening 204 into lumen 102. In some embodiments, the proximal end of inner tube lumen 202 is fluidly connected to pump unit 300.

In some embodiments, outer tube member 100 and inner tube member 200 are substantially coaxial, such that outer lumen 102 extends annularly around the entirety of the exterior wall surface of inner tube member 200. In other embodiments, at least a portion of the exterior wall surface of inner tube member 200 is connected to or in contact with a portion of the interior wall surface of outer tube member 100.

Figures 2A, 2B:
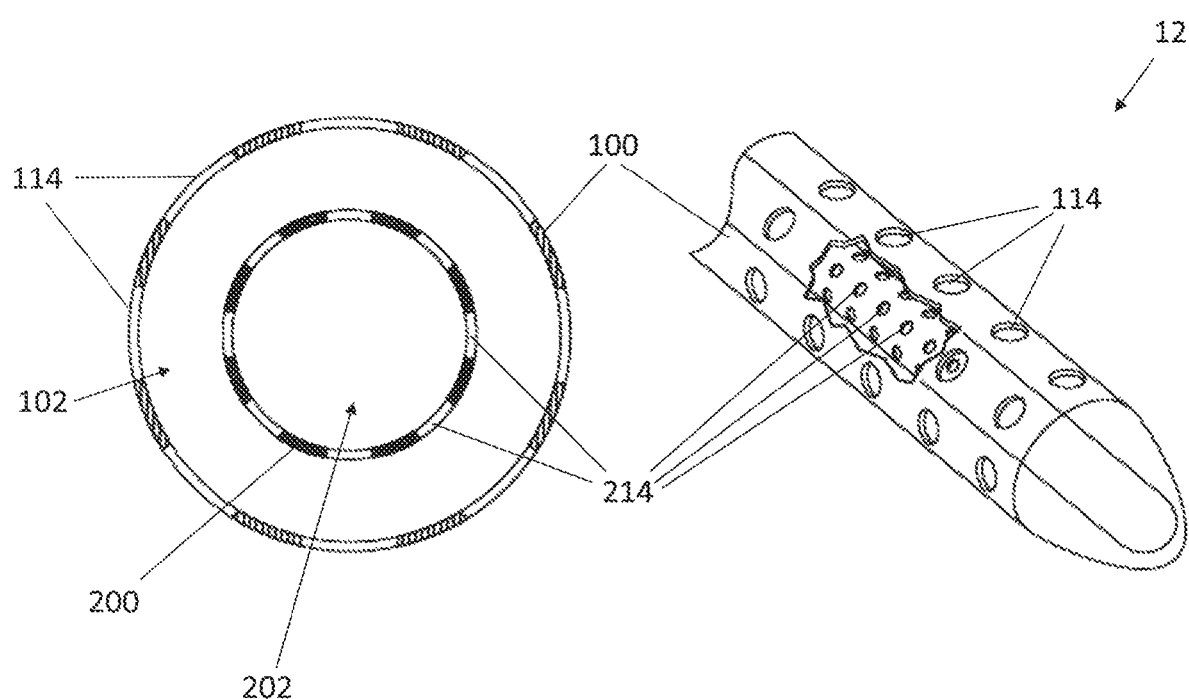
FIG. 2A depicts a cross sectional view of the distal portion of an exemplary embodiment of a cerebral shunt device.
FIG. 2B depicts a perspective view of the distal end of an exemplary embodiment of the cerebral shunt and a cutaway allowing for visualization of the plurality of holes in the inner tube member.

There is no limitation to the particular size of device 10. For example, in one embodiment, the diameter of the outer lumen can be in a range of 2.2 to 2.7 mm, such as about 2.5 mm. In another embodiment, the diameter of the inner lumen can be in a range of 0.3 to 0.8 mm, such as about 0.5 mm. In one embodiment the length of the device is in the range of 10 cm to 20 cm, and preferably, approximately 14 cm, with the pump unit 300 adding an additional 1 cm to 5 cm in length, preferably approximately 2.5 cm. In some embodiments, at least the distal ends of outer and inner tube members 100 and 200, respectively, include one or more openings leading into the outer lumen 102, 202 of each tube member 100, 200. In some embodiments, these openings are only in the distal region 12 of device 10. In other embodiments, the openings 114, 214 are additionally positioned in a middle region of device 10. In other embodiments, the openings are additionally positioned in a proximal region of device 10. In still other embodiments, the openings are positioned anywhere along the length of device 10. For example, as shown in FIG. 2B, the distal end 12 of outer tube member 100 may include at least one, and preferably a plurality of holes 114 sized such that they are capable of drawing fluids, for example cerebral spinal fluid, into outer lumen 102 of outer tube member 100 from the cerebral ventricular space of the subject in a manner suitable for drainage of the cerebral ventricle.

There is no limitation to the number of holes 114, or the pattern of holes 114 at distal end 12 of outer tube member 100. For example, the number of holes 114 positioned around the circumference of the outer tube member 100 can be in the range of 4-10. In one embodiment, the number of holes 114 positioned around the circumference of the outer membrane 100 is six. In some embodiments, holes 114 are sized such that CSF can freely pass through the holes but cells such as cells of the choroid plexus are restricted from passing into outer lumen 102. Likewise, distal end 12 of inner tube member 200 may include at least one, and preferably a plurality of holes 214 sized such that they are capable of delivering a suitable gas, liquid or other fluid from inner tube lumen 202 of inner tube member 200 into outer lumen 102 of outer tube member 100. There is no limitation to the number of holes 214, or the pattern of holes 214 at the distal end of inner tube member 200. In some embodiments, the number of holes 214 positioned around the circumference of the inner tube member 200 can be in the range of 8-12. In one embodiment, the number of holes 214 positioned around the circumference of the inner membrane 200 is ten. In some embodiments, holes 214 are sized such that gaseous fluids such as air can freely pass through the holes, but liquid fluids such as CSF have limited or no transport across holes 214. For example, in some embodiments, holes 214 are sized such that only pressurized air or other gas is capable of passing therethrough. In other embodiments, holes 214 are sized such that air or other gas types are capable of passing through, and the targeted liquid being drained may also pass through when a threshold pressure is generated in inner tube lumen 202. In still other embodiments, holes 214 may be sized such that liquid may pass therethrough, albeit at a slower rate than the passage of liquid through holes 114. In some embodiments, holes 114 are generally circular and can be in the range of about 0.5-1 mm in diameter, more preferably holes 114 are about 0.6 mm in diameter. In some embodiments, holes 214 are also generally circular and can be in the range of about 0.2-0.6 mm in diameter, more preferably holes 214 are about 0.3 mm in diameter. In still other embodiments, inner tube member 200 does not include any holes along its length, and instead is constructed of an expandable material. In such embodiments, when pump unit 300 drives a fluid into inner lumen 202, inner tube member 200 expands, thereby reducing the space within outer lumen 102 and generating the desired pressure in outer lumen 102 to temporarily reverse the flow of CSF back through holes 114 to dislodge the obstructing debris.

Figure 3:
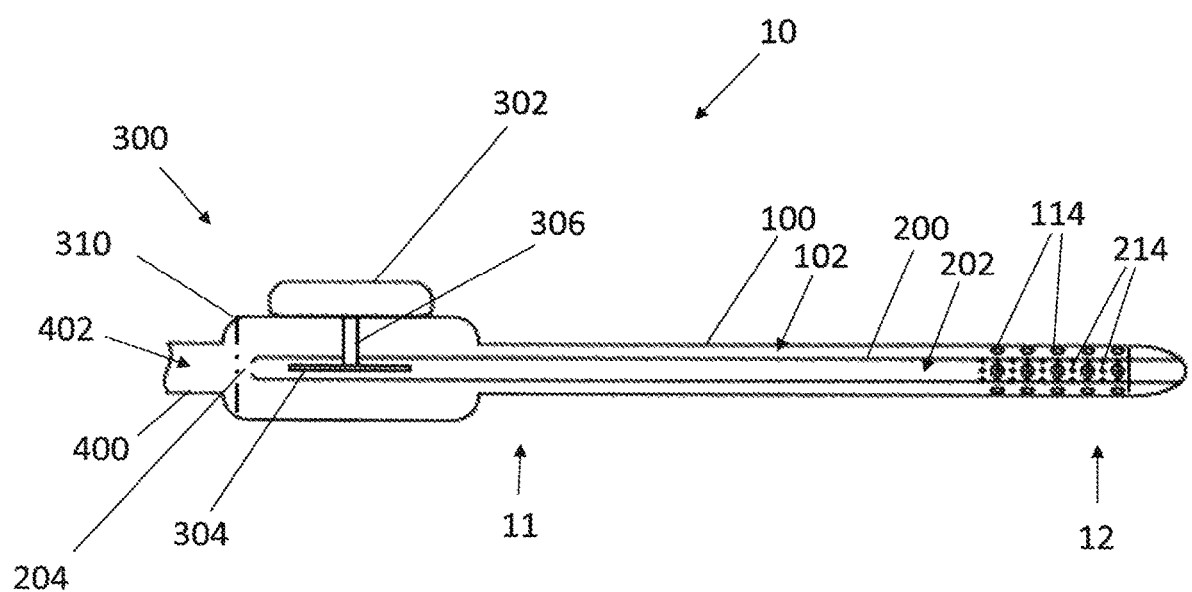
FIG. 3 is a side view of an exemplary embodiment of cerebral shunt device having a controller and its components, the inner tube member and inner lumen, and the outer tube member and outer lumen.

Referring now to FIG. 3, a side view of the cerebral shunt device is depicted. As contemplated herein, pump unit 300 is positioned on the proximal end 11 of cerebral shunt device 10 and generally includes a pump 302, a circulating member 304 and a conduit 306. Device 10 may further include a valve 310 positioned between drainage tube 400 and pump unit 300. The pump unit 300 and components of the pump unit may be a variety of sizes. Embodiments may be between 1 cm and 5 cm, larger or smaller, and in one embodiment is approximately 2.5 cm in length.

Pump 302 may be any suitable compressor or pump for increasing the pressure in inner lumen 202. In some embodiments, pump 302 is an air pump capable of driving air or another gas into inner lumen 202 to generate pressure. In other embodiments, pump 302 is a hydraulic pump capable of driving a liquid into inner lumen 202 to generate pressure. In some embodiments, pump 302 is directly connected to device 10 (as shown in FIG. 3), while in other embodiments, pump 302 may be separate from device 10, with conduit 306 extending from pump unit 300 of device 10 to wherever pump 302 is separately positioned. In some embodiments, pump 302 comprises a sterile filtering means, for example a filter with a pore size of about 0.2 µm, about 0.45 µm, and/or the like. In some embodiments, pump 302 circulates air contained within inner lumen 202.

The pump 302 may be powered by any number of means, including a battery. The battery may be a rechargeable battery, rechargeable by wireless means. This feature would be especially useful because the patient would not have to visit the hospital to check the power level of the battery, as they could check the battery level themselves. Battery levels and other diagnostics may be checked by pairing the device with handheld devices such as Apple® or Android® phones, or can be another handheld device such as a watch or other gadget. The handheld device can have the capacity to warn patients of critically low battery levels, whereby the patient could change the battery themselves by pressing a battery release button. The battery may incorporate features such as being a self-charging battery, as are known the art. The device may include at least one control factor that the user has the ability to control via the handheld, or other device. The at least one control factor may be transmitted to an app on a handheld device or other devices, and included, but are not limited to: CSF pressure, flow of the CSF, power level of the pump 302, speed of the circulating member 304 (and abilities to control speed via the app). The device may also include sensors that detect the level of circulating choroid plexus and debris in the ventricle of the brain.

Conduit 306 fluidly connects pump 302 to inner lumen 202. In some embodiments, circulating member 304 is also connected to the walls of conduit 306. In some embodiments, all or a portion of conduit 306 rotates with circulating member 304. In some embodiments, all or a portion of conduit 306 is fixed in one or more positions. In some embodiments, conduit 306 may include a one-way valve to prevent any backflow of air or liquid to pump 302.

Circulating member 304 may include any number of rotating blades or saddles that rotate about an axis perpendicular to the inner and outer lumens to promote directional flow of air and/or liquid passing through inner lumen 202. In some embodiments, pump unit 300 may include a motor to drive circulating member 304.

In some embodiments, pump unit 300 also includes a feedback sensor for detecting the pressure within inner lumen 202, such that pump 302 can shut off or reduce output when a threshold pressure is detected in inner lumen 202. In some embodiments, pump unit 300 may include a flow sensor. In some embodiments, pump unit 300 may include a flow regulator. In some embodiments, pump unit 300 may include a power source and a controller or computer processing unit for storing data, receiving signals and sending instructional signals to/from one or more sensors, valves or regulating components. Such features in generic pumps are well known in the art. In such embodiments, the controller or processing unit may be communicatively connected (wired or wirelessly) to any computing device, such as a smartphone, so that device 10 can send data to the computing device for display, and operational instructions can likewise be sent from the computing device to device 10.

In some embodiments, cerebral shunt device 10 may also include a valve 310 positioned within the proximal region of outer lumen 102. Valve 310 may be any suitable valve for regulating flow of a fluid, such as a one-way valve, ball valve, gate valve, butterfly valve, plug valve, globe valve, punch valve, check valve, and the like.

Valve 310 may be communicatively connected to a controller or processing unit, if present, such that valve 310 may be partially or fully opened and closed based on signals received from the controller or processing unit. As contemplated herein, valve 310 may be opened and closed to regulate fluid flow from outer tube lumen 102 to drainage tube 400. For example, when device 10 is drawing a targeted fluid through holes 114 into outer lumen 102 to be drained, valve 310 may be in a fully or partially open position so that the fluid passes through valve 310 into drainage tube 400. Then, when holes 114 become obstructed by debris, valve 310 is capable of moving to a closed position, so that pressure within inner and outer lumens 202 and 102 can be increased via activation of pump unit 300.

In traditional existing cerebral shunts, the valve is a separate component that is attached between the ventricular catheter and the distal catheter. However, in the present embodiments described, there is no need for a separate valve since the power generated circulating member 304 prevents backflow of CSF from the distal end 12 of the device as it forces the flow of the CSF in a forward direction. In the present embodiments, valve 310 has been included in case CSF were to flow backwards at a time when the circulating member 304 were to stop for a brief period of time, since the circulating member's 304 speed would be adjusted based on the CSF flow, CSF pressure, and the amount of choroid plexus or debris present in the ventricle.

In some embodiments, cerebral shunt device 10 also includes a mechanism for aspirating fluid from outer tube lumen 102, for example an aspiration syringe, a vacuum pump, or any other mechanism for creating a syphon, may be used to actively pull liquid through holes 114 into outer lumen 102. This aspirating mechanism may form part of pump unit 300, or may be fluidly connected to drainage tube 400. In some embodiments, device 10 may include a fluid collecting reservoir connected to drainage tube 400 for collecting and/or disposing the drained fluid. In some embodiments, the drained fluid may be returned to one or more regions within the subject.

In some embodiments, cerebral shunt device 10 includes an anchoring mechanism for attaching device 10 to the subject, such as by suture, clip, adhesive, etc., to decrease unwanted movement of device 10 when implemented in a subject. As contemplated herein, cerebral shunt device 10 may be constructed from any suitable material known in the art used in the construction of shunts, and particularly shunts suitable for insertion into the cerebral ventricle of a subject. That is, device 10 is constructed from any suitable material known in the art that is flexible enough to be positioned around anatomical structures of the ventricle space, while being rigid and incompressible enough to be inserted into the ventricle space by means such as applied pressure and/or tension. For example, outer tube member 100 may be constructed from any suitable material known in the art that is flexible enough to navigate anatomical structures of the ventricle space while being rigid and incompressible enough to be positionable within the ventricle space using means such as applied pressure and/or tension. Outer tube member 100 is also rigid and impressible enough to maintain a fluid clearance in outer lumen 102 while cerebral shunt device 10 is positioned within the ventricle space. Accordingly, outer tube member 100 may be constructed from one or more suitable polymeric materials including silicone, thermoplastic material, such as polyethylene block amide copolymer, polyvinyl chloride, polyethylene, polyethylene terephthalate, polyamide, polyurethane and/or a thermoset polymer, such as polyimide. In some embodiments, inner tube member 200 is constructed from any suitable material known in the art that is flexible enough to allow device 10 to be positioned around anatomical structures of the ventricle space while being rigid and incompressible enough to reinforce the structure of outer tube member 100 during placement into and use within the ventricle space. In some embodiments, inner tube member 200 may be expandable, and therefore be constructed of an expandable material. Likewise, inner tube member 200 may be constructed from one or more suitable polymeric materials including silicone, thermoplastic material, such as polyethylene block amide copolymer, polyvinyl chloride, polyethylene, polyethylene terephthalate, polyamide, polyurethane and/or a thermoset polymer, such as polyimide. Any standard manufacturing technique, such as extrusion or injection molding, may be used to construct the structural, housing components of device 10 as would be understood by those skilled in the art. In some embodiments, all or a portion of outer and/or inner tube members may optionally be reinforced with a wire, mesh or other framework to add additional support to the tube structure.

Methods of Use

The present embodiments also relate to methods for enhancing proper drainage of fluid from a bodily space, an in particular, CSF from the ventricle space of a subject by maintaining the free flow of draining CSF. For example, as outlined in FIG. 4, a method 500 of implanting and using present embodiments may include the steps of inserting the distal region of a cerebral shunt device described herein into the cerebral ventricle of a subject 510, positioning one or more of the drainage holes of the outer lumen tube within a region of the ventricle space 520, and drawing CSF through the outer lumen holes and into the outer lumen of the device to flow proximally from the ventricle into the drainage tube 530. Upon obstruction of flow through the holes of the outer tube member, the method further includes the steps of activating the pump unit to drive a fluid (e.g., air and/or CSF) into the inner lumen of the device to generate pressure within the inner lumen, which subsequently increases the pressure within the outer lumen enough that flow of CSF is temporarily reversed back through the holes of the outer lumen (or the fluid pumped from the pump unit is pushed through the holes of the outer lumen), thereby dislodging any obstructions to the free flow of fluid into the outer lumen 540.

Accordingly in step 540, activating the pump unit generates a pressure within the inner and outer lumens of the device to push the CSF out into the outer lumen by creating a high pressure in the inner lumen. This process pushes the debris and the choroid plexus away from the pores on the outer lumen, thus preventing the undesired blockage. Lastly is the step of deactivating the pump unit to again permit flow of fluid (e.g. CSF) through the outer lumen holes and into the outer lumen of the device to flow proximally from a space (e.g. the ventricle) into the drainage tube 550. In some embodiments, the cerebral shunt is introduced into the ventricle space of a subject through a peripheral incision. In one embodiment, the method comprises the step of inserting the catheter using a guidance mechanism, for example, but not limited to, a guide wire, an X-ray guidance system, an ultrasound guidance system.

Figures 5A, 5B, 5C:
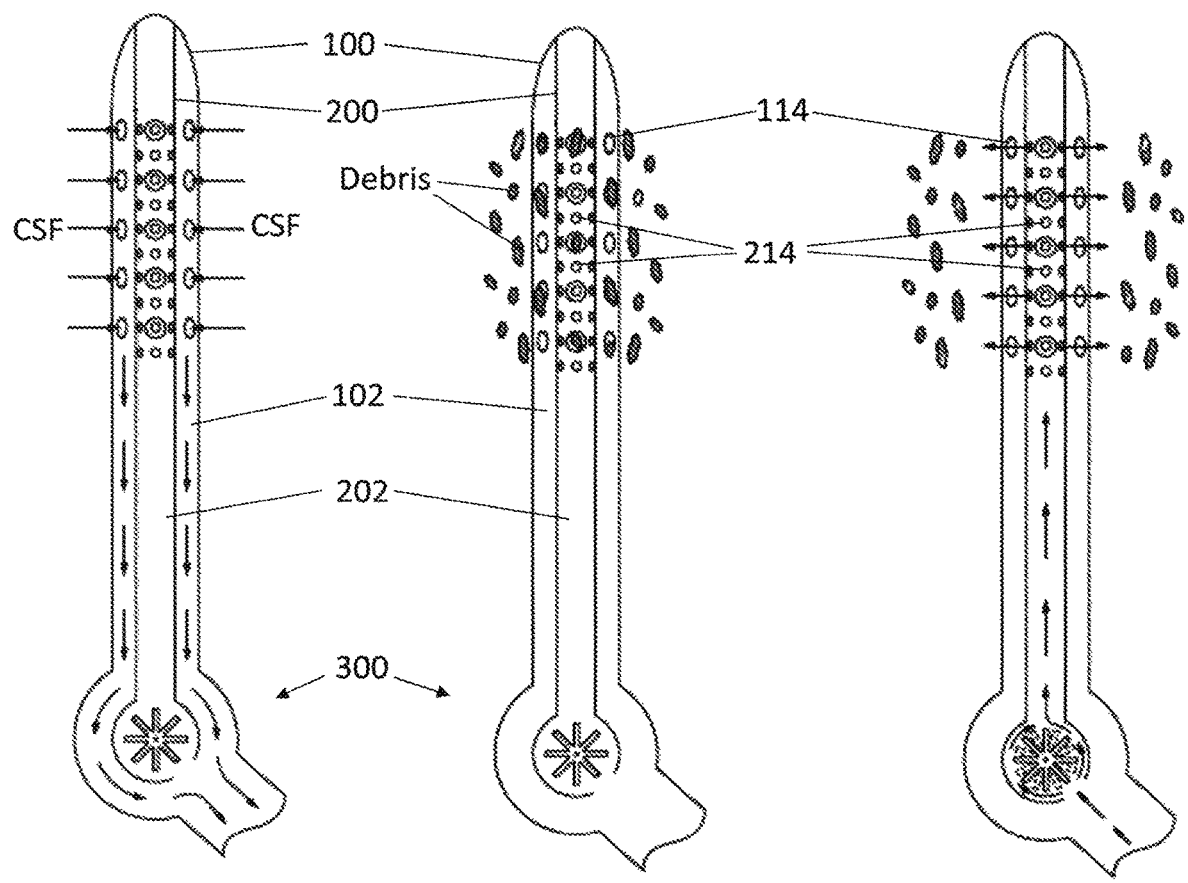
FIG. 5A is a cross-sectional view of an exemplary embodiment of a cerebral shunt where fluid if freely flowing into the outer lumen through the holes in the outer tube member, and is draining proximally into a proximal catheter.
FIG. 5B is a cross sectional view of a scenario where the holes in the outer tube member of a cerebral shunt become clogged, thereby obstructing flow into the outer lumen.
FIG. 5C is cross-sectional view of scenario where the controller is activated to pump air distally through the inner lumen and through the holes at the distal end of the inner tube member, thereby generating an increase in pressure in the distal end of the outer lumen and forcing air and fluid out through the holes in the outer tube member to clear the debris blocking the holes in the outer tube member.

Referring now to FIGS. 5A-5C, the device 10 is depicted at various stages of use. As shown in Figure SA, during normal operation, CSF flows freely into outer lumen 102 through outer lumen holes 114, and may or may not enter inner lumen 202 through inner lumen holes 214. As shown in FIG. 5B, flow may be obstructed by debris such as cells and other materials from the choroid plexus that may clog outer lumen holes 114, thereby preventing CSF from freely flowing into outer lumen 102. As illustrated in FIG. 5C, when obstruction of CSF flow is detected, the pump unit 300 is activated to drive fluid intermittently into inner lumen 202, such that pressure is generated in inner lumen 202 until fluid passes through inner lumen holes 214 into outer lumen 102 to generate enough pressure in outer lumen 102 to either drive the pumped fluid or reverse the flow of CSF through outer lumen holes 114 to dislodge any debris from the exterior surface blocking holes 114. In some embodiments, closure of valve 310 is activated when pump unit 300 is activated to more quickly achieve the desired pressure within the inner and outer lumens 202 and 102. In some embodiments, positive pressure is applied by pump unit 300 for a fixed or set period of time. The disclosures of each and every patent, patent application, and publication cited herein are hereby incorporated herein by reference in their entirety.

The device 10 has numerous advantageous features over present day shunt devices, as described above. In particular, the use of two tube members 100, 200 unlike previous device that only use a single tube. The presence of two tube members 100, 200 allows increased and better flow of CSF through the device. In addition, the power generated circulating member (turbine) 304, controls the flow of CSF, and prevents backflow, which normally would be accomplished by a valve (as used in prior devices). However, the present embodiments do not require a valve to prevent backflow because the circulating member 304 directs and forces fluid in a direction that prevents backflow and obstructions. The ability to control the flow of CSF and fluid pressure allows for controlled prevention of obstruction in the shunt in a superior manner compared to current shunts.

The following reference numerals are used throughout FIGS. 1-5:
- 10 Cerebral shunt device
- 11 Proximal end of device
- 12 Distal end (or region) of device
- 100 Outer tube member
- 102 Outer lumen/Outer tube lumen
- 114 Holes (openings) at distal end of outer tube (outer lumen holes)
- 200 Inner tube member
- 202 Inner tube lumen
- 204 Inner tube opening
- 214 Holes (openings) at distal end of inner tube (inner lumen holes)
- 300 Pump unit
- 302 Pump
- 310 Valve (positioned within the proximal region of the outer lumen
- 304 Circulating member (e.g. turbine)
- 306 Conduit connecting pump to inner lumen
- 400 Drainage tube
- 402 Lumen of the drainage tube
- 500 Method (steps) of implanting an using the shunt
- 510 Inserting shunt into subject
- 520 Positioning draining holes within region of ventricle space
- 530 Drawing CSF through outer lumen openings into outer lumen
- 540 Activating pump to generate pressure to push CSF to outer lumen
- 550 Deactivating pump to reduce pressure and permit drawing of CSF through outer lumen openings and into the outer lumen While the embodiments have been described in terms of exemplary embodiments, it is to be understood that the words that have been used are words of description and not of limitation. As is understood by persons of ordinary skill in the art, a variety of modifications can be made without departing from the scope of the invention defined by the following claims, which should be given their fullest, fair scope.

What is claimed is:

1. A method of removing fluid from a subject, comprising the steps of:
   (a) providing a shunt device, the shunt device having
      (i) an outer tube member forming a first lumen, the outer tube member having a drainage outlet and at least one opening to the first lumen in a distal region along a length of the outer tube member;
      (ii) an inner tube member forming a second lumen, the inner tube member having at least one opening to the second lumen along the length of the inner tube member, wherein the inner tube member is positioned within the first lumen;
      (iii) a pump unit fluidly connected to the second lumen; and,
      (iv) at least one flow sensor;
      wherein the shunt device is a cerebral shunt device;
   (b) inserting the distal region of the shunt device into a bodily space of a subject;
   (c) positioning the at least one opening along the length of the outer tube member within a region of the bodily space;
   (d) drawing fluid from bodily space through the at least one opening along the length of the outer tube member and into the first lumen;
   (e) upon determining that the at least one opening along the length of the outer tube member is obstructed, activating the pump unit to inject a fluid into the second lumen to generate enough pressure within the first lumen to force the fluid from the first lumen out through the at least one opening along the length of the outer tube member, thereby clearing the obstruction; and
   (f) deactivating the pump unit to permit drawing the fluid from a bodily space through the at least one opening along a length of the outer tube member and into the first lumen.

2. The method of claim 1, wherein the pump unit is activated at a set time interval.

3. The method of claim 1, wherein the fluid is cerebrospinal fluid.

4. The method of claim 1, wherein the fluid is cerebrospinal fluid and the bodily space is ventricle space.

5. The method of claim 1, further comprising the steps of: monitoring at least one control factor, and controlling flow of the fluid based at least in part on monitored control factor.

* * * * *